United States Patent [19]

Marsh

[11] 4,115,384
[45] Sep. 19, 1978

[54] N-CYANOAZIRIDINES

[75] Inventor: Frank Dennis Marsh, Wilmington, Del.

[73] Assignee: E. I. Du Pont de Nemours and Company, Wilmington, Del.

[21] Appl. No.: 687,176

[22] Filed: May 17, 1976

Related U.S. Application Data

[60] Continuation-in-part of Ser. No. 501,457, Aug. 28, 1974, division of Ser. No. 832,423, Jun. 11, 1969, Pat. No. 3,849,465, which is a division of Ser. No. 383,233, Jul. 16, 1964, Pat. No. 3,510,474.

[51] Int. Cl.$^2$ .................. C07D 203/26; C07D 203/02; C07D 203/12
[52] U.S. Cl. ................................................. 260/239 E
[58] Field of Search ..................................... 260/239 E

[56] References Cited

U.S. PATENT DOCUMENTS

| 3,510,474 | 8/1970 | Marsh | 260/239 E |
| 3,849,465 | 11/1974 | Marsh | 260/551 C |

OTHER PUBLICATIONS

Jackson et al., Brit. J. Pharm. 14, 149–157, (1959).
Lukes et al., Chem. Abs. 51, 1949f, (1957).
Pala et al., J. Med. Chem. 14, 174–175, (1971).
Hermes et al., J. Org. Chem. 37, 2969, (1962).

*Primary Examiner*—Donald G. Daus
*Assistant Examiner*—Mark L. Berch
*Attorney, Agent, or Firm*—Anthony P. Mentis

[57] ABSTRACT

N-Cyanoaziridines containing the grouping

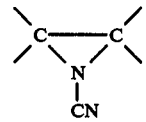

are obtained by reacting an ethylenically unsaturated compound with cyanogen azide (N$_3$CN). Exemplary is 3-cyanoazatricyclo[3.2.1.0$^{2,4}$] octane of the formula

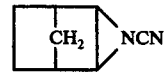

obtained by reacting norbornene with N$_3$CN.

10 Claims, No Drawings

N-CYANOAZIRIDINES

RELATED APPLICATION

This application is a continuation-in-part of my copending application Ser. No. 501,457 filed Aug. 28, 1974 now abandoned, which is a division of application Ser. No. 832,423 filed June 11, 1969 now U.S. Pat. No. 3,849,465; which was a division of application Ser. No. 383,233 filed July 16, 1964 now U.S. Pat. No. 3,510,474; which in turn was a continuation-in-part of Ser. No. 234,878 filed Nov. 1, 1962, now abandoned.

BACKGROUND OF THE INVENTION

1. Field of the Invention

This invention relates to N-cyanoaziridines.

2. Prior Art

Brigl, Berichte, vol. 45, page 1557 (1912) purports to show an N-cyanoimine in formula II. He rejects it as not representing the compound he prepared from cyanamide and acetoacetic ester.

Goldberg and Golov, Reactions of Cyanamide and Ketones, Khim. Nauka i Prom. 4, 138 (1959); C.A. vol. 53, col. 16953 (1959) purport to show the preparation of N-cyanoimines by reaction of cyanamide with ketones. The reaction products have an indeterminate structure, however, and are not the compounds of the invention.

No prior art appears to exist with respect to N-cyanoaziridines.

WARNING: Cyanogen azide is explosive when free or nearly free of solvent and should then be handled with great care. It can be used, however, with comparative safety in dilute or moderately concentrated solution.

DESCRIPTION OF THE INVENTION

The novel products of this invention are derived from the reaction of cyanogen azide ($N_3CN$) with an ethylenically unsaturated compound. The products vary in complexity from comparatively simple compounds obtained by reaction of a single molecule of cyanogen azide with a molecule of a monomeric compound containing a single ethylenic linkage to polysubstituted products obtained by reaction of a number of cyanogen azide molecules with a monomeric molecule containing a plurality of ethylenic linkages. The basic reaction in all instances is the same, however, and results in the formation of products containing one or more of the characteristic groups,

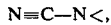

wherein the dangling valences are attached either to two separate adjoining carbons of an organic group thereby forming an N-cyanoaziridine, i.e., a compound containing an N-cyanoazacyclopropyl group, or to a single carbon of an organic group to form an N-cyanoimine. In the reaction of cyanogen azide with a monoethylenic compound, a mixture of N-cyanoaziridine and N-cyanoimine is generally formed, whereas in the addition of cyanogen azide to compounds containing two or more ethylenic groups, the products may contain both N-cyanoaziridine and N-cyanoimine groups in the same molecule.

The reactants are employed in essentially equimolar proportions. There is nothing critical about these proportions, however, and one or the other reactant can be present in excess. With polyethylenically unsaturated compounds the reaction with cyanogen azide can be controlled to take place at part or all of the ethylenic double bonds, depending upon the ratio of the reactants and conditions of reaction selected. If, for example, the reactant is a diolefin and it is desired to effect reaction at both double bonds, at least two moles of the cyanogen azide will be needed per mole of the diolefin; if the reactant is a triolefin and it is desired to effect reaction at all three double bonds, at least three moles of cyanogen azide will be needed per mole of triolefin.

When the organic compound is a liquid under the conditions of reaction, it can be used both as reaction medium and reactant. When a separate reaction medium is used, it should be one which is normally liquid and substantially inert toward the reactants and reaction products at the reaction temperature employed. It is therefore to be understood that the medium in any one instance must be selected with due consideration of the reaction conditions to be used. Suitable reaction media for many olefins are propionitrile, acetonitrile, ethyl acetate, amyl acetate, 1,2-dimethoxyethane, dimethylformamide, 1,1,2,2-tetrachlorethane, isooctane, methylene chloride, carbon tetrachloride, and 1,2-dibromoethane.

The nature of the reaction between cyanogen azide and the organic compound depends upon whether the latter is saturated or ethylenically unsaturated. With ethylenically unsaturated compounds, the reaction occurs at low temperature, i.e., below 50° C., essentially exclusively at the double bonds with virtually no attack at carbon-hydrogen bonds.

The aziridines of the invention have the formula

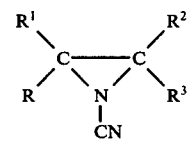

wherein the R's (R, $R^1$, $R^2$ and $R^3$) individually are members of the group consisting of hydrogen, halogen, nitro, cyano, alkoxy, aryloxy, alkylsilyl, alkylthio, acyl, acyloxy, carboxyl, carbamoyl, N-hydrocarbylcarbamoyl, hydrocarbyloxycarbonyl, e.g., alkoxycarbonyl, hydrocarbyl, including alkyl, aryl, aralkyl, alkylaryl, cycloalkyl, and alkenyl, and substituted hydrocarbyl groups containing one or more of the previously mentioned groups as substituents, e.g., haloalkyl, haloaryl, hydroxyalkyl, hydroxyaryl, cyanoalkyl, cyanoaryl, alkoxyalkyl, and alkoxyaryl, said R's individually containing up to 18 carbons; any two R's may be joined together to form an alkylene or oxygen-interrupted alkylene group of up to 14 carbons; with the proviso that only one of R, $R^1$, $R^2$ and $R^3$ is nitro.

Preferred aziridines, because of the ready availability of the ethylenic reactants, are those where the R groups, taken individually are hydrogen or hydrocarbyl containing up to 18 carbons in which any unsaturation is ethylenic, with the proviso that any two of the R groups can be joined together to form an alkylene or cycloalkylene group of up to 14 carbons.

A wide variety of monomeric ethylenically unsaturated compounds can be reacted with cyanogen azide in preparing the N-cyanoaziridines of this invention. The ethylenic compound can be monoethylenic or polyethylenic, cyclic or acyclic, and substituted or unsubstituted. When the ethylenic compound contains one or more substituents, i.e., when it is not wholly hydrocarbon, such substitutent, if electron withdrawing, is preferably at least one carbon removed from the ethylenically unsaturated carbon atoms. There is no preference or restriction for the location of electron-donating substituents as reactions proceed readily whatever the relative position of the substituent with respect to the ethylenically unsaturated carbon. Some polymerization of the ethylenic compound may occur as a side reaction, particularly in the case of readily polymerizable vinyl compounds.

Examples of simple monomeric monoethylenic compounds which can be used include ethylene, propylene, 3-phenyl-1-propene, butene-1, butene-2, isobutylene, hexenes, octenes, dodecenes, octadecenes, 1,2-dimethylcyclopropene, cyclobutene, cyclopentene, methylenecyclobutane, methylcyclopentene, methylenecyclopentane, methylenecyclohexane, cyclohexene, cycloheptene, cyclodecene, cyclododecene, vinylcyclohexane, bicycloheptene, styrene, p-ethylstyrene, β-vinylnaphthalene, stilbene, and substituted monoethylenic compounds, such as allyl bromide, allyl alcohol, allyl acetate, allyl phenol, vinyl chloride, vinyl fluoride, vinylidene chloride, vinylidene fluoride, tetrafluoroethylene, vinyl methyl ketone, allyl phenyl ether, vinyl ethyl ether, vinyl phenyl ether, dihydrofuran, dihydropyran, vinyl ethyl sulfide, vinyl acetate, vinyl butyrate, nitroethylene, 3-nitro-1-propene, p-nitrostyrene, acrylonitrile, methacrylonitrile, 1,4-dicyanobutene-2, allyl cyanide, acrylic acid, crotonic acid, maleic acid, cinnamic acid, ethyl crotonate, butyl acrylate, benzyl acrylate, methyl methacrylate, acrylamide, N-diethyl acrylamide, m-iodostyrene, p-cyanostyrene, o-hydroxystyrene, o-methoxystyrene, and 2(β,β-dicyano-α-hydroxyvinyl)-4-methylphenol (U.S. Pat. No. 2,726,249).

Typical examples of dienes and other polyenes that can be used as the ethylenic reactant are butadiene, isoprene, chloroprene, 2,4-hexadiene, diallyl, cyclopentadiene, dicyclopentadiene, tetracyclopentadiene, vinyl cyclohexene, divinyl ether, 1,5-cyclooctadiene, and 1,3,5-hexatriene.

The unsaturated reactants are substituted and unsubstituted ethylenic (i.e., olefinic) hydrocarbons of the formula R(R¹)C=C(R²) (R³), particularly those of 2–12 carbons. Halogen, cyano, hydroxy, carboxyl, alkoxy, and alkoxy carbonyl are the preferred substituents for the substituted hydrocarbon reactants.

EMBODIMENTS OF THE INVENTION

There follow some examples which are intended to illustrate, but not to limit, the invention. Some examples show isolation of the principal product only, whereas others, where both the N-cyanoaziridine and the N-cyanoimines are formed in substantial amounts, show the isolation of both products.

EXAMPLE 1

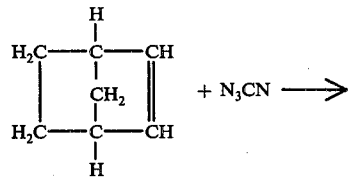 + N₃CN ⟶

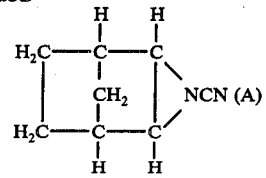

(principal product)

A flask equipped with a wet-ice condenser, magnetic stirrer, gas-inlet tube, and nitrogen bubbler was assembled, flame-dried and cooled to ambient temperature under nitrogen. Sodium azide (19.5 g, 0.3 mole, sieved through a 60 mesh screen) was added and the flask cooled in a carbon dioxide-acetone bath. Cyanogen chloride (115 g, 1.87 mole) was condensed into the flask and allowed to warm to reflux temperature for 24 hours under nitrogen. Bicyclo[2.2.1]hept-2-ene (50 g, 0.54 mole) was then added slowly and the mixture refluxed (ca. 16°–18° C.) for about 20 hours, during which time nitrogen was liberated. The mixture was then heated to 55° C. to remove excess cyanogen chloride, cooled to ambient temperature, and then diluted with 50 cc (39.6 g) of dry acetone. The mixture was filtered under nitrogen to separate sodium chloride and the solvent removed from the filtrate on a rotary evaporator at 0.3 mm/50° C. thereby leaving 5 g of product mixture. This mixture consisted of approximately 80% of the N-cyanoaziridine, 3-cyanoazatricyclo[3.2.1.0²,⁴]octane, shown in formula A above, and 20% of the N-cyanoalkylideneimine, bicyclo[2.2.1]-heptane-2-N-cyanoimine, formula B, below:

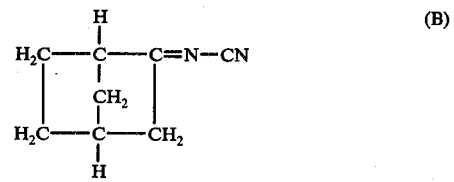

The components of the above mixture (5 g) were separated and identified as follows: The mixture was passed over a column packed with 160 g of a neutral hydrous alumina. The column was eluted with benzene, and the solvent was evaporated yielding a colorless, mobile liquid whose infrared spectrum was the same as that of the starting material, except for the following:

(a) The original band at 6.1μ (>C=N) was absent.
(b) A new band appeared at 5.75μ (>C=O).

The new band was attributed to norcamphor from the hydrolysis of the bicyclo[2.2.1]heptan-2-N-cyanoimine (compound B). Distillation of the chromatographed mixture removed the volatile norcamphor which was isolated and identified as its 2,4-dinitrophenylhydrazone derivative, melting point 130° C. The 5.75μ band was absent in the remaining liquid. The remainder of the spectrum was unchanged. This material was assigned the structure of compound A, 3-cyanoazatricyclo[3.2.1.0²,⁴]octane.

The structure of the N-cyanoaziridine derivative was further verified by reduction with lithium aluminum hydride as follows:

To 300 ml. of dry diethyl ether in a 500-ml flask, equipped with a magnetic stirrer and drying tube, 3 g (0.08 mole) of lithium aluminum hydride was added.

The mixture was stirred at room temperature for 24 hours, and there was then added 2.5 g. (0.02 mole) of the adduct of cyanogen azide with bicyclo[2.2.1]hept-2-ene in 35 ml of diethyl ether over a period of 30 minutes. The reaction mixture was stirred for 26 hours at room temperature and was then decomposed with a saturated solution of sodium sulfate. The inorganic salts were removed by filtration and the filtrate evaporated to yield 2.3 g. of a mobile amine-smelling liquid. The nitrile band (4.5μ) in the infrared spectrum was essentially absent.

To 900 mg. of the amine obtained was above in 7 ml of cyclohexane there was added 2 g. (0.015 mole) of phenyl isothiocyanate. The exothermic reaction which ensued was cooled in an ice bath and the resultant solid triturated with 40 ml of cyclohexane. It was then filtered to yield 1.3 g of a product melting at 100°–113° C. Recrystallization from ethanol or benzene in petroleum ether mixture gave white needles melting at 116°–118° C.

The infrared and nuclear magnetic resonance spectra were in accord with the structure of 3-azatricyclo[3.2.1.0$^{2,4}$]octane-3-thiocarboxanilide:

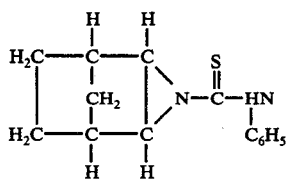

Anal. Calcd. for $C_{14}H_{16}SN_2$: C, 68.8; H, 6.6; N, 11.5; S, 13.12. Found: C, 68.86; H, 6.68; N, 11.33; S, 13.23; C, 68.86; H, 6.72; N, 11.39; S, 13.47.

EXAMPLE 2

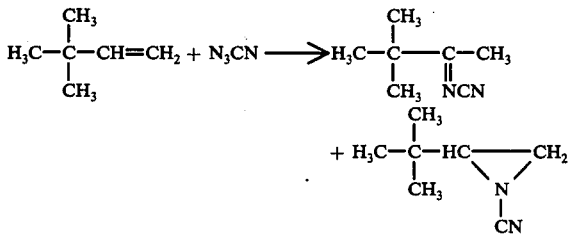

To a solution of cyanogen azide prepared as described in Example 3 from activated sodium azide (19.50 g, 0.3 mole) and cyanogen chloride (67 g, 1.1 mole) in acetonitrile (120 (120 ml, 93.5 g, 2.28 mole) was added 3,3-dimethyl-1-butene (57 g, 0.68 mole). The mixture was heated at 34°–43° C. for 15 hours, during which time ca. 0.3 mole of nitrogen was liberated. Continued heating at this temperature for 1½ additional hours caused no further nitrogen evolution. After cooling to room temperature the mixture was diluted with ether, filtered, and the solvent and excess olefin removed in a rotary evaporator at 0.3 mm and room temperature. There remained 35.61 g (95.5% yield) of a light tan mobile oil. Distillation of this oil through a molecular type still at 0.3 mm gave 29.58 g (79.4% yield) of mixture of isomers consisting of ca. 74% 2,2-dimethyl-3-N-cyanoiminobutane and 26% 2-tertiary butyl-1-N-cyanoaziridine. Fractionation of 22.78 g of this material through 17 in × 8 mm spinning band column separated pure 2,2-dimethyl-3-N-cyanoiminobutane. Infrared and nmr analysis of the lower boiling fractions indicated that it contained major amounts of 2-tertiary butyl-1-cyanoaziridine.

EXAMPLE 3

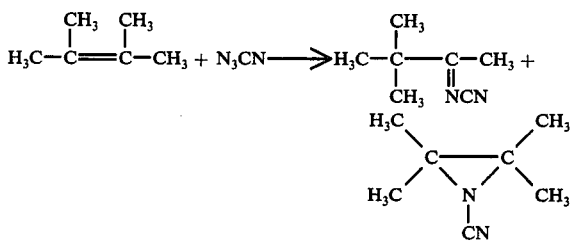

A 500-ml flask equipped with an ice-cooled condenser, magnetic stirrer, dropping funnel, nitrogen bubbler, and gas-inlet tube was assembled, flame-dried, and cooled to ambient temperature under nitrogen. Sodium azide (32.5 g, 0.5 mole) and dry acetonitrile (200 ml, 156 g) were added and the flask cooled in an ice-salt bath. Cyanogen chloride (80 ml, 97.4 g, 1.58 mole) was distilled into the reaction mixture over a period of 1¾ hours at such a rate as to maintain the temperature between 4°–18° C. When addition was complete, the reaction mixture was warmed to 25° C. and 2,3-dimethyl-2-butene (88.25 g, 1.05 mole) was added rapidly through the dropping funnel. During a reaction period of 14 hours at 30°–38° C., ca. 0.5 mole of nitrogen evolved. Heating at this temperature was continued for an additional two hours. The mixture was cooled to room temperature, diluted with ether (100 ml, 71.4 g), filtered, and the solvent removed from the filtrate on a rotary evaporator at 0.3 mm and room temperature. There remained 60.65 g (98% yield) of a mixture of isomeric products. Distillation of the total product through a molecular type still at 0.1 mm and a bath temperature of 32°–47° C. gave a colorless oil (60.34 g, 97.2% yield) consisting of ca. 92% 2,2-dimethyl-3-N-cyanoiminobutane and 8% 1-cyano-2,2,3,3-tetramethylaziridine as determined by nmr spectra Fractionation of 31.7 g aliquot of this oil through a 17 in × 8 mm spinning band column separated pure 2,2-dimethyl-3-N-cyanoiminobutane (bp 38°–40° C./0.05 mm; $n_D^{25}$, 1.4570).

Anal. Calcd. for $C_7H_{12}N_2$: C, 67.69; H, 9.74; N, 22.56. Found: C, 68.07; H, 9.85; N, 23.02.

A slightly lower boiling fraction (bp 36° C./0.03 mm; $n_D^{25}$, 1.4561) consisted predominantly of 1-cyano-2,2,3,3-tetramethylaziridine.

Anal. Calcd. for $C_7H_{12}N_2$: C, 67.69; H, 9.74; N, 22.56. Found: C, 67.92; H, 9.73; N, 22.61. 2,2-Dimethyl-3-N-cyanoiminobutane was identified by infrared and nmr spectra and by hydrolysis to pinacolone and cyanimide. 1-Cyano-2,2,3,3-tetramethylaziridine was identified by its characteristic unsplit resonance at −83 cps relative to tetramethylsilane.

EXAMPLE 4

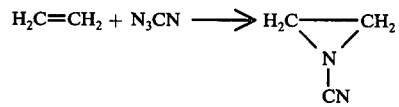

An acetonitrile solution (55 ml) containing 13.6 g (0.02 mole) of cyanogen azide was placed in a 240-ml nickel-molybdenum-iron alloy-lined tube and pressured with 18 g (0.64 mole) of ethylene. The tube was held at 21°–27° C. for 20 hours, during which time the internal pressure rose from 480 psi to 740 psi. The resulting solution was poured into 500 ml of ether and about 3 g of polymeric material was removed by filtration. After the filtrate was evaporated to 5.5 g the residue was distilled through a short path still at a pot temperature of 30°–35° C./0.2 mm to give about 2 g (15%) of 1-cyanoaziridine, a colorless oil.

Anal. Calcd. for $C_3H_4N_2$: C, 52.9; H, 5.9; N, 41.2. Found: C, 51.8; H, 5.9; N, 41.3.

Infrared analysis of this product showed strong absorption at 4.50μ (—C≡N) and 6.80μ, 6.90μ (—CH$_2$), with no absorption at 6.0–6.2μ characteristic of the

group, and none at 7.2–7.4μ (—CH$_3$). The n-m-r spectrum shows only one absorption at $\tau = 7.53$.

EXAMPLE 5

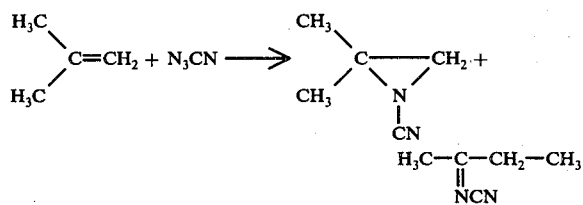

To 80 ml nickel-molybdenum-iron alloy-lined pressure vessels were charged with 6.5 g (0.1 mole) of sodium azide and 20.3 g (26 ml) of acetonitrile, and to each was added 12 g (0.20 mole) of cyanogen chloride and 16 g (0.29 mole) of isobutylene. After the tubes were shaken for 20 hours at 35°–36° C., the contents were removed, combined, filtered to remove the salt, and the filtrate was evaporated to remove volatile material. Distillation through a molecular-type still gave 50% yield of a mixture of 2,2-dimethyl-1-cyano-aziridine and 2-N-cyanoiminobutane, boiling at a pot temperature of 40°–50° C./0.25 mm.

Anal. Calcd. for $C_5H_8N_2$: C, 62.5; H, 8.4; N, 30.1. Found: C, 62.3; H, 8.1; N, 29.8 C, 62.1; H, 8.2.

In a similar experiment carried out at 26°–27° C., an 82% yield of the $C_5H_8N_2$ mixture was obtained, which was shown by n-m-r to be 41% 2,2-dimethyl-1-cyanoaziridine and 59% 2-N-cyanoiminobutane.

If the above reaction is repeated using benzene as the medium, the mixture consists of 77% 2-N-cyanoiminobutane and 23% 2,2-dimethyl-1-cyanoaziridine. With ethyl acetate as the medium, the mixture consists of 54% 2-N-cyanoiminobutane and 46% 2,2-dimethyl-1-cyanoaziridine.

In a duplication of the first of the above experiments, the isomer mixture was distilled through a 24 in × 8 mm spinning band column and an essentially pure sample of 2,2-dimethyl-1-cyanoaziridine was obtained, bp 24°–25° C./0.4 mm; $n_D^{25}$, 1.4422.

Anal. Calcd. for $C_5H_8N_2$: C, 62.5; H, 8.4. Found: C, 62.7; H, 8.2.

The nmr spectrum showed a sharp singlet at $\tau = 8.57$ for the methyl groups and a singlet at $\tau = 7.66$ for the methylene protons.

From this same distillation was obtained essentially pure 2-N-cyanoiminobutane, bp 30° C./0.4 mm; $N_D^{25}$, 1.4517.

The nmr of the 2-N-cyanoiminobutane shows absorption at $\tau = 8.72, 8.83, 8.96,$ and $7.20, 7.32, 7.43$ (7.56) for the ethyl group and $\tau = 7.58$ and $7.71$ for the stereoisomeric syn-cyanomethyl group and anti-cyanomethyl group, respectively.

EXAMPLE 6

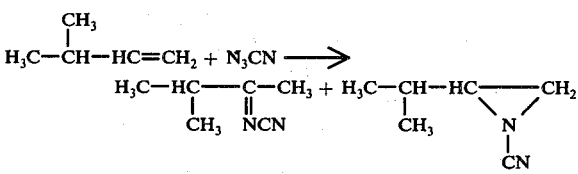

Each of two 80 ml nickel-molybdenum-iron alloy-lined tubes was charged with 6.5 g (0.1 mole) of sodium azide and 20.3 g (26 ml) of acetonitrile, cooled, and to each was added 12 g (0.20 mole) of cyanogen chloride and 20 g (0.29 mole) of 3-methyl-1-butene. The sealed tubes were heated at 23°–40° C. for 19 hours, after which the combined products were filtered to remove sodium chloride. The filtrate was concentrated on a rotating evaporator and distillation through a 24 in × 8 mm spinning band column gave a 41% yield of a crude mixture of 3-methyl-2-cyanoiminobutane and 2-isopropyl-1-cyanoaziridine, along with 36% of polymeric residue.

The first fraction from the distillation had a boiling point of 38°–39° C./0.35 mm and was shown by nmr to be about 90% 2-isopropyl-1-cyanoaziridine, while higher boiling fractions, bp 42° C./0.40 mm, were shown to be nearly pure 3-methyl-2-N-cyanoiminobutane.

In a similar experiment at 26°–27° C., an 86% yield of the isomer mixture was obtained.

EXAMPLE 7

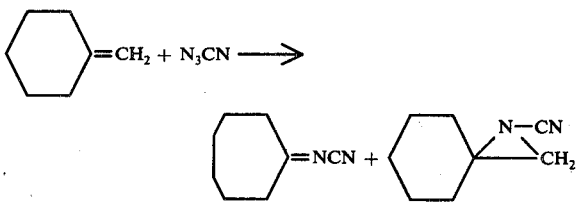

An acetonitrile solution (29 ml) containing 6.8 g (0.1 mole) of cyanogen azide was added to 20 g (0.21 mole) of methylenecyclohexane (shown to be pure by gas chromatography). Nitrogen was liberated readily and over a period of 9 hours 1.99 l. of nitrogen (80%) was obtained, with a reaction temperature of 22°–28° C. After removal of solvent and excess methylenecyclohexane on a rotating evaporator, 11.75 g of crude product (87%) was obtained. Distillation at a pot temperature of 96°–103° C./1 mm gave 8.30 g (61%) of a mixture of 1-cyanoiminocycloheptane and 1-cyano-2-cyclopentamethyleneaziridine; $n_D^{25}$, 1.4880 to 1.5026.

Anal. Calcd. for $C_8H_{12}N_2$: C, 70.5; H, 8.9; N, 20.6. Found: C, 70.5; H, 8.7; N, 20.2; C, 70.5; H, 8.9; N, 20.4.

Proton magnetic resonance analysis indicated that the mixture contained 71% of the cyanoiminocycloheptane and 29% of the aziridine. This ratio changes with change or reaction medium, e.g., in ethyl acetate solution, 61% 1-cyanoiminocycloheptane and 39% of aziridine are formed while in benzene solution, 82% of cyanoiminocycloheptane and 18% of aziridine are produced.

The above process was repeated using 5 g (0.05 mole) of methylenecyclohexane, 25 ml. of dimethylformamide, and 1.7 g (0.025 mole) of cyanogen azide. After 16 hours at 25° C. there was obtained 2 g of an oil which was shown by nmr spectroscopy to be pure 1-cyanoiminocycloheptane containing no 1-cyano-2-cyclopentamethyleneaziridine.

The above process was again repeated using 5 g of methylenecyclohexane dissolved in 10 ml of acetic acid and a small amount of 2.5 molar cyanogen azide in ethyl acetate at 40° C. After evaporation of the solvents and excess reactants, an oil was obtained whose nmr spectrum indicated that it was 100% 1-cyano-2-cyclopentamethyleneaziridine containing no 1-cyanoiminocycloheptane.

EXAMPLE 8

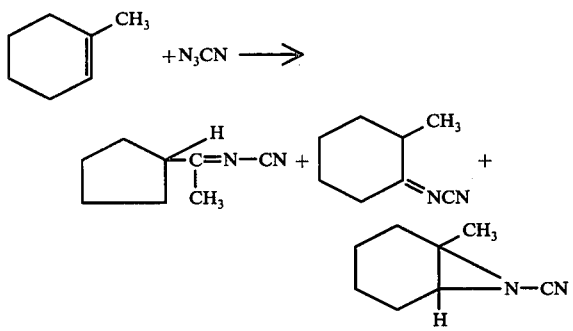

Forty milliliters of acetonitrile solution containing 10.2 g (0.15 mole) of cyanogen azide was added to 24 g (0.25 mole) of 1-methylcyclohexane, and over a 23.5-hour period 2.48 l. (66%) of nitrogen was evolved. After evaporation of the solvent, the crude product was investigated by nmr spectroscopy and three compounds were identified as constituents: 1-cyanoimino-2-methylcyclohexane, 45%; 1-(1-N-cyanoiminoethyl)cyclopentane, 25%; and 1-cyano-2-methyl-2,3-cyclohexanylaziridine, 17%. Distillation of the mixture through a short path still at a pot temperature of 39°-77° C./0.05–0.10 mm gave 7.23 g (35%) of the isomer mixture.

Anal. Calcd. for $C_8H_{12}N_2$: C, 70.6; H, 8.9; N, 20.6. Found: C, 70.3; H, 9.7; C, 70.2; H, 9.6.

EXAMPLE 9

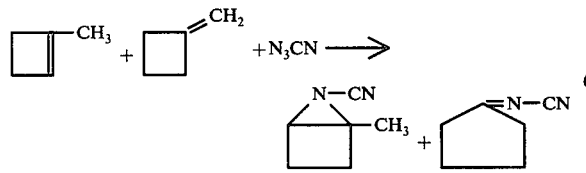

The reaction of cyanogen azide with methylenecyclobutane containing 6% 1-methylcyclobutene at room temperature gave predominantly 1-cyanoiminocyclopentane; however, nmr spectroscopy strongly indicates that a small amount of 1-cyano-2-methyl-2,3-cyclobutanylaziridine is present in the isomeric $C_6H_8N_2$ mixture.

EXAMPLE 10

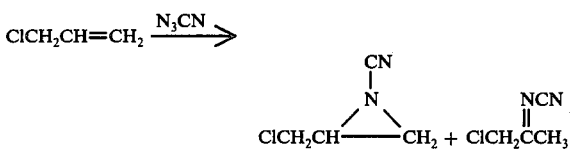

A solution of 1.9 g (2.8 mmoles) of cyanogen azide in 1 ml of carbon tetrachloride was added to 0.11 g (1.4 mmole) of allyl chloride, and the mixture was allowed to stand for 2 hours at ambient temperature. The magnetic resonance spectra of the resulting solution was determined using a Varian high resolution nmr spectrometer and electromagnet at a frequency of 30 mc and a field of 7500 gauss. The nmr spectrum indicated that presence of both 1-cyano-2-chloromethylaziridine and 2-cyanoimino-3-chloropropane.

EXAMPLE 11

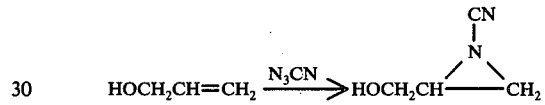

Allyl alcohol (0.08 g, 1.4 mmole) was treated with cyanogen azide in carbon tetrachloride and the mixture allowed to stand for two hours at ambient temperature. The nmr spectrum of the resulting solution indicated the presence of 1-cyano-2-hydroxymethylaziridine in the reaction product.

EXAMPLE 12

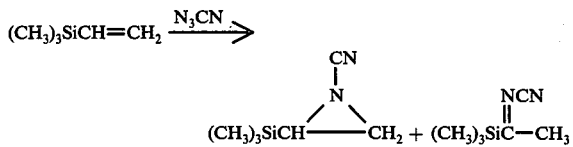

Trimethylvinyl silane (0.1 g, 1.4 mmole) was treated to cyanogen azide in carbon tetrachloride according to the procedure of Example 12. The nmr spectrum of the product mixture indicated that both 1-trimethylsilyl-1-cyanoiminoethane and 1-cyano-2-trimethylsilylaziridine were present in the product mixture.

EXAMPLE 13

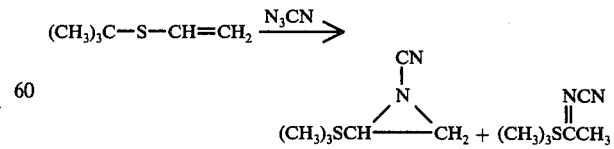

A cyanogen azide solution containing 0.19 g (2.81 mmole) in 1 ml of carbon tetrachloride was added to 0.1 g (1 mmole) of tertiary butyl vinyl sulfide according to the procedure of Example 22. The nmr spectrum of the product indicated presence of both 1-cyanoimino-1-tertiary butylthioethane and 1-cyano-2-tertiary butyl thioaziridine.

EXAMPLE 14

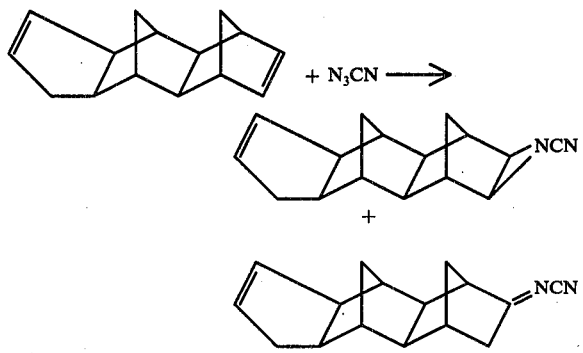

A solution of cyanogen azide (0.15 mole) in acetonitrile (88 ml) was added to a slurry of tricyclopentadiene (3a,4,4a,5,8,8a,9,9a-octahydro-4,9:5,8-dimethanol-1H-cyclopenta[b]naphthalene, 29.7 g, 0.15 mole) in acetonitrile (75 ml) at such a rate that the temperature remained between 20° and 35° C. After 2 hr., 0.15 mole of nitrogen had evolved. The mixture was filtered to separate an off-white crystalline product (29.2 g, 82%, mp 155°–160°). The filtrate was concentrated to give additional product (3.3 g) for a total of 32.5 g (91%). The compound was recrystallized from acetonitrile to give pure 2,8:3,7-dimethanocyclopenta[6,8]naphth[2,3-b]aziridine-1-carbonitrile, 1,1a,2,2a,3,3a,6,6a,7,7a,8,8-decahydro (mp 162°–164°).

Anal. Calcd for $C_{16}H_{18}N_2$: C, 80.64; H, 7.61; N, 11.76. Found: C, 80.90; H, 7.95; N, 11.76; C, 80.76; H, 7.76; N, 11.96.

Infrared $\lambda_{max}^{KBr}$ 3.26 μ (=CH), 3.37 μ, 3.44 μ and 3.48 μ (saturated CH); 4.54 μ (—NCN), 6.22 μ (C↑C).

H nmr (CDCl$_3$) 5.58 (2H complex group, vinyl protons), 3.08 (3H singlet, two aziridine ring protons and one tertiary allyl proton), 2.57 (3H broad singlet, unassigned), 0.5–2.5 (10H complex group, unassigned).

EXAMPLE 15

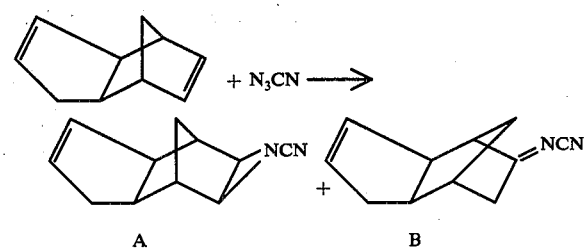

Cyanogen azide in acetonitrile (1.7 molar, 118 ml) was added during 1 hr to dicyclopentadiene (1,4-dihydro-1,4-methanonaphthalene; 26.4 g, 0.2 mole). The reaction was very exothermic and the temperature rose to 65° at one point. Nitrogen (5.17 l) was liberated. The mixture was evaporated to dryness to give an oil (36 g) which crystallized on standing at room temperature. The crude mixture was distilled to give a mixture of A and B (totalling 22.8 g, 66%) which was identified by its infrared and H nmr spectra.

In a subsequent experiment cyanogen chloride was distilled at 1 g/min. into an agitated slurry of dicyclopentadiene (1,4-dihydro-1,4-methanonaphthalene; 66 g, 0.5 mole), 32.5 g (0.5 mole) of sodium azide, and 300 ml of acetonitrile. The initial temperature was 25° and the reaction was maintained below 30° by ice cooling. After 45 g (~ 0.75 mole) of cyanogen chloride was added, the mixture was allowed to stand for 5 hr after which 12.4 l. of nitrogen had evolved (99%). The mixture was filtered and the filtrate treated with ethyl alcohol (150 ml) and 10% aqueous ammonium chloride (150 ml). After 1 hr, the organic solvents were removed under reduced pressure and the water layer was extracted with ether. The ether extract was washed with water, then aqueous sodium bisulfite and finally water, and was then dried over magnesium sulfate and the ether removed on a rotary evaporator. Crystalline product (74 g, 85%) resulted which was recrystallized from 5:1 hexane-ether to give pure product (mp 69.8°–70.2°) which may be named 1,1a,2,2a,5,5a,6,6a-octahydro-2,6-methanoindeno[5,6-b]aziridine-1-carbonitrile.

H nmr 6.9 (doublet J = 5 cps), 7.2 (1H doublet J = 5 cps, 6.8 (1H multiplet, bridgehead CH), 9.1 (1H antidoublet, J = 10 cps methano bridge CH), 8.5 (1H syn doublet J = 10 cps), 4.3 (2H multiplet, vinyl protons, 6.9–7.9 (5H unassigned).

EXAMPLE 16

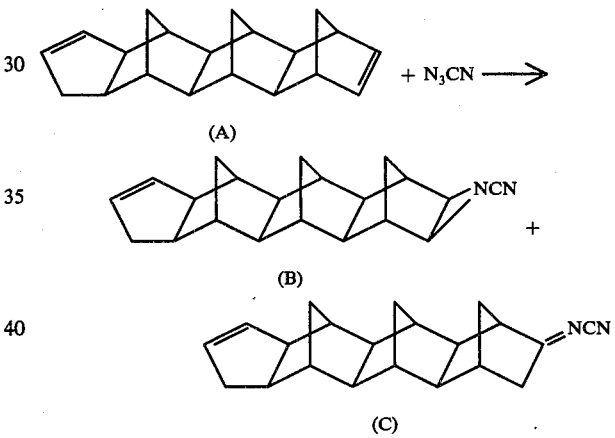

If one reacts tetracyclopentadiene (A) with one equivalent of cyanogen azide following the procedure given in example 14, one will obtain predominantly (B) (1,1a,2,2a3,3a,4,4a,7,7a,8,8a,9,9a,10,10a-hexadecahydro-2,10:3,9:4,8-trimethano-cyclopenta[6,7]anthra[2,3-b]aziridine-1-carbonitrile with smaller amounts of (C) (3a,4,4a,5,5a,6,7,8,9,9a,10,10a,11,11a-tetradecahydro[4,11:5,10:6,9-trimethano-1-H-cyclopent[b]anthracen-7-ylidene]cyanamide.

EXAMPLE 17

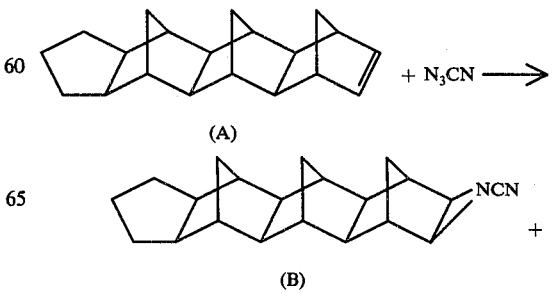

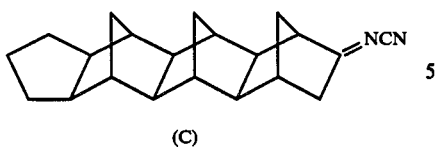

(C)

If one reacts a partially reduced tetracyclopentadiene (A) with one equivalent of cyanogen azide following the procedure given in example 14, one will obtain as the main product (B) (1,1a,2,2a,3,3a,4,4a,5,6,7,7a,8,8a,9,9a,10,10-octadecahydro-2,10:3,9:4,8-trimethanocyclopent[6.7]anthra[2,3-b]aziridine-1-carbonitrile with smaller amounts of (C) (2,3,3a,4,4a,5,5a,6,7,8,9,9a,10,10a,11,11a-hexadecahydro[3,11:5,10:6,9-trimethano-1-Hcyclopenta[b]-anthracene-7-ylidene]cyanamide.

The products obtained from monomeric ethylenically unsaturated compounds are useful as adhesives for bonding neoprene to itself, to natural rubber, and to other substrates. For example, one-eighth inch thick strips of neoprene and natural rubber were firmly joined by pressing a small sample of 2,2-dimethyl-1-cyanoaziridine, prepared as in Example 5, between them and heating at 100° C. and 4000 psi for 2 minutes.

N-Cyanoaziridines are readily reduced with lithium aluminum hydride to the aziridines in good yield and the latter are useful as cross-linking agents, insect sterilants, photographic inhibitors and discoloration inhibitors in polymers.

Since obvious modifications and equivalents will by evident to those skilled in the chemical arts, I propose to be bound solely by the appended claims.

I claim:

1. An N-cyanozairidine of the formula

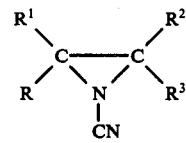

the R's taken individually are hydrogen or alkyl having up to 18 carbons, and any two of the R groups can be joined together to form an alkylene or cycloalkylene group of up to 14 carbons or one of the R's is trimethylsilyl.

2. A compound of claim 1 which is 3-cyanoazatricyclo[3.2.1.0$^{2,4}$] octane.

3. A compound of claim 1 which is 2-tertiary butyl-1-N-cyanoaziridine.

4. A compound of claim 1 which is 1-cyano-2,2,3,3-tetramethylaziridine.

5. A compound of claim 1 which is 1-cyanoaziridine.

6. A compound of claim 1 which is 2,2-dimethyl-1-cyanoaziridine.

7. A compound of claim 1 which is 2-isopropyl-1-cyanoaziridine.

8. A compound of claim 1 which is 1-cyano-2-cyclopentamethyleneaziridine.

9. A compound of claim 1 which is 1-cyano-2-methyl-2,3-cyclohexanylaziridine.

10. A compound of claim 1 which is 1-cyano-2-methyl-2,3-cyclobutanylaziridine.

* * * * *